US012758379B1

(12) United States Patent
Malek et al.

(10) Patent No.: US 12,758,379 B1
(45) Date of Patent: Oct. 13, 2026

(54) METHOD OF INJECTION MOLDING A BREAST IMPLANT AND RELATED APPARATUS

(71) Applicant: Marcel Malek, Scottsdale, AZ (US)

(72) Inventors: Marcel Malek, Scottsdale, AZ (US); Allen Moore, Cary, NC (US); Joshua Fisher, Raleigh, NC (US); Russell Turner, Hillsborough, NC (US)

(*) Notice: Subject to any disclaimer, the term of this patent is extended or adjusted under 35 U.S.C. 154(b) by 90 days.

(21) Appl. No.: 18/463,177

(22) Filed: Sep. 7, 2023

(51) Int. Cl.

| | |
|---|---|
| ***A61F 2/12*** | (2006.01) |
| ***B29C 33/38*** | (2006.01) |
| ***B29C 33/76*** | (2006.01) |
| ***B29C 45/26*** | (2006.01) |
| ***B33Y 50/00*** | (2015.01) |
| ***B33Y 80/00*** | (2015.01) |
| *B29L 31/00* | (2006.01) |

(52) U.S. Cl.
CPC ............ *A61F 2/12* (2013.01); *B29C 33/3842* (2013.01); *B29C 33/76* (2013.01); *B29C 45/26* (2013.01); *B33Y 50/00* (2014.12); *B33Y 80/00* (2014.12); *A61F 2240/004* (2013.01); *B29L 2031/7532* (2013.01)

(58) Field of Classification Search
CPC ..... A61F 2/12; A61F 2240/004; B33Y 50/00; B33Y 80/00; B29C 33/3842; B29C 33/76; B29C 45/26; B29L 2031/7532
USPC ........................................................ 264/40.1
See application file for complete search history.

(56) References Cited

U.S. PATENT DOCUMENTS

| | | | |
|---|---|---|---|
| 5,480,430 A | 1/1996 | Carlisle et al. | |
| 6,086,801 A * | 7/2000 | Eaton ...................... | B29C 39/02 264/225 |
| 6,146,418 A | 11/2000 | Berman | |
| 6,605,116 B2 | 8/2003 | Falcon et al. | |
| 9,399,122 B2 | 7/2016 | Mosharrafa et al. | |
| 9,463,087 B2 | 10/2016 | Hristov et al. | |
| 9,700,405 B2 | 7/2017 | Davila et al. | |
| 10,617,516 B2 | 4/2020 | Davila et al. | |
| 10,898,313 B2 | 1/2021 | Feinberg et al. | |
| 11,160,630 B2 | 11/2021 | Schuessler et al. | |
| 11,357,614 B1 | 6/2022 | Malek | |

(Continued)

FOREIGN PATENT DOCUMENTS

| | | |
|---|---|---|
| FR | 2826255 | 12/2002 |
| WO | 1995001864 | 1/1995 |

OTHER PUBLICATIONS

International Search Report, PCT Patent Application No. PCT/US2022/72327, Aug. 3, 2022, 2 pages.

*Primary Examiner* — Christina A Johnson
*Assistant Examiner* — Xue H Liu
(74) *Attorney, Agent, or Firm* — IPTechLaw

(57) ABSTRACT

Implementations of methods of injection molding a breast implant may include placing a core within an outer mold having a cavity. The cavity may correspond in shape and size to a breast implant. The method may include injecting a molding into a volume between the core and outer mold, removing the molding from the core and outer mold, and filling the molding to form the breast implant. A first thickness of the volume between the core and the outer mold around a perimeter of the core at a vertex boundary may be greater than a second thickness of the volume between the core and the outer mold at a cusp of the core.

13 Claims, 8 Drawing Sheets

(56) References Cited

U.S. PATENT DOCUMENTS

| | | | | |
|---|---|---|---|---|
| 2003/0134067 | A1* | 7/2003 | Garelli | B29C 45/435 425/437 |
| 2003/0205846 | A1 | 11/2003 | Bellin et al. | |
| 2004/0127985 | A1 | 7/2004 | Bellin et al. | |
| 2007/0135916 | A1 | 6/2007 | Maxwell et al. | |
| 2009/0240342 | A1 | 9/2009 | Lindh, Sr. et al. | |
| 2010/0178414 | A1 | 7/2010 | Judge et al. | |
| 2012/0165934 | A1 | 6/2012 | Schuessler et al. | |
| 2013/0231743 | A1 | 9/2013 | Becker | |
| 2014/0039617 | A1 | 2/2014 | Maxwell et al. | |
| 2015/0272722 | A1 | 10/2015 | Davila et al. | |
| 2016/0082235 | A1 | 3/2016 | Mosharrafa et al. | |
| 2016/0228236 | A1 | 8/2016 | Egnelöv et al. | |
| 2016/0331513 | A1 | 11/2016 | Brown et al. | |
| 2017/0224869 | A1 | 8/2017 | Shah et al. | |
| 2018/0064530 | A1 | 3/2018 | Glicksman | |
| 2019/0015194 | A1 | 1/2019 | Bocca | |
| 2019/0142574 | A1 | 5/2019 | Quirós et al. | |
| 2020/0046489 | A1 | 2/2020 | Feinberg et al. | |
| 2020/0100892 | A1 | 4/2020 | Limem et al. | |
| 2020/0345476 | A1 | 11/2020 | Wang et al. | |
| 2020/0397554 | A1 | 12/2020 | Van Epps et al. | |
| 2021/0346150 | A1 | 11/2021 | Quirós et al. | |
| 2022/0371229 | A1* | 11/2022 | Klein | B29C 64/124 |

* cited by examiner

METHOD OF INJECTION MOLDING A BREAST IMPLANT AND RELATED APPARATUS

BACKGROUND

1. Technical Field

Aspects of this document relate generally to methods of forming breast implants. More specific implementations involve methods of injection molding breast implants.

2. Background

Breast implants are prostheses used to change the shape and appearance of a breast. Breast implants may be used in either aesthetic or reconstructive surgeries. Breast implants may be formed by dipping a mandrel into liquid silicon and allowing the liquid silicon to then dry.

SUMMARY

Implementations of methods of injection molding a breast implant may include placing a core within an outer mold having a cavity. The cavity may correspond in shape and size to a breast implant. The method may include injecting a molding into a volume between the core and outer mold, removing the molding from the core and outer mold, and filling the molding to form the breast implant. A first thickness of the volume between the core and the outer mold around a perimeter of the core at a vertex boundary may be greater than a second thickness of the volume between the core and the outer mold at a cusp of the core.

Implementations of methods of injection molding a breast implant may include one, all, or any of the following:

The cavity may correspond in shape and size to a round breast implant.

The cavity may correspond in shape and size to a teardrop shaped breast implant.

The cavity may include a smooth sidewall configured to form a smooth breast implant.

The method may include smoothing the breast implant after removing the molding from the core and the outer mold.

The method may include placing the molding into a cradle prior to filling the molding and attaching a back-fill jig to the molding.

A back portion of the core may include a channel.

Implementations of methods of injection molding a breast implant may include scanning an intended recipient of a breast implant and 3D printing a customized core, based on the intended recipient, configured to be placed within an outer mold comprising a cavity. The cavity may correspond in shape and size to a breast implant. The method may include placing the customized core into the cavity, injecting a molding into a volume between the customized core and outer mold, removing the molding from the customized core and outer mold, and filling the molding to form the breast implant. The customized core may include a back portion opposite a front portion. The back portion may be divided from the front portion by a vertex boundary. A thickness of the volume between the customized core and outer mold may vary depending upon the intended recipient.

Implementations of methods of injection molding a breast implant may include one, all, or any of the following:

The cavity may correspond in shape and size to a round breast implant.

The cavity may correspond in shape and size to a teardrop shaped breast implant.

The outer mold may be made from steel.

The method may include smoothing the breast implant after removing the molding from the customized core and the outer mold.

The back portion of the customized core may include a channel.

Implementations of breast implant injection molds may include an outer mold including a cavity and a core configured to be in the cavity. The core may include a back surface opposite a front surface. The back surface may include a flat surface. The core may include a vertex boundary that divides the back surface from the front surface. When the core is in the cavity, a volume is formed between the core and cavity. A first thickness of the volume between the core and the outer mold around a perimeter of the core at the vertex boundary may be greater than a second thickness between the core and the outer mold at a cusp of the volume.

Implementations of the injection mold may include one, all, or any of the following:

The breast implant injection mold is a round breast implant injection mold.

The breast implant injection mold is a teardrop shaped breast implant injection mold.

The back surface of the core may include a channel.

The back surface of the core may include two intersecting channels.

A thickness of the volume between the core and outer mold at the cusp of the volume may transition from a greater thickness to a lesser thickness.

A third thickness of the volume between the core and the outer mold along the entire back surface of the core is greater than a fourth thickness of the volume between the core and the outer mold at the front surface of the mold.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended method of injection molding a breast implant and breast implant injection molds will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such methods of injection molding breast implants, breast implant injection molds, and implementing components and methods, consistent with the intended operation and methods.

Figure 1:
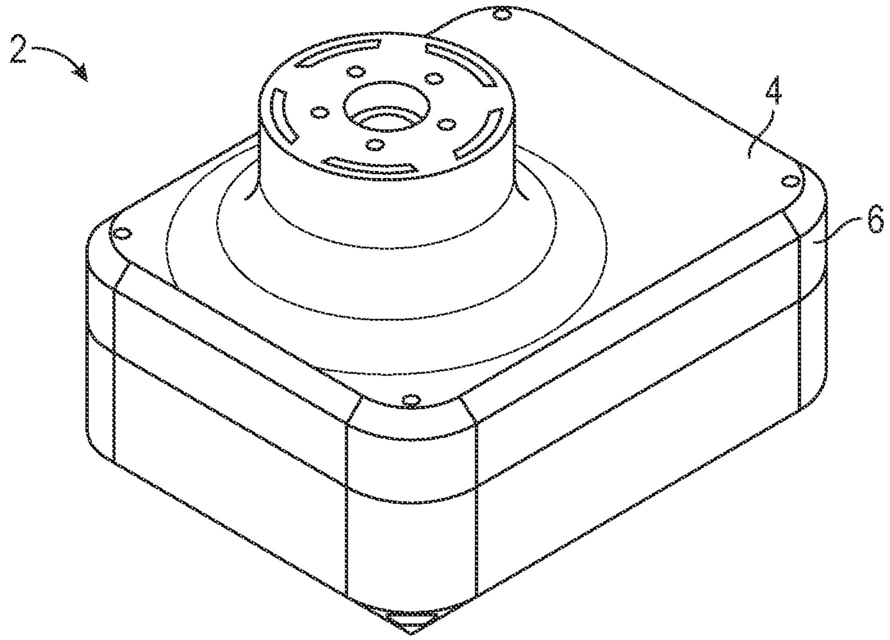
FIG. 1 is a perspective view of a breast implant injection mold.
Figure 2:
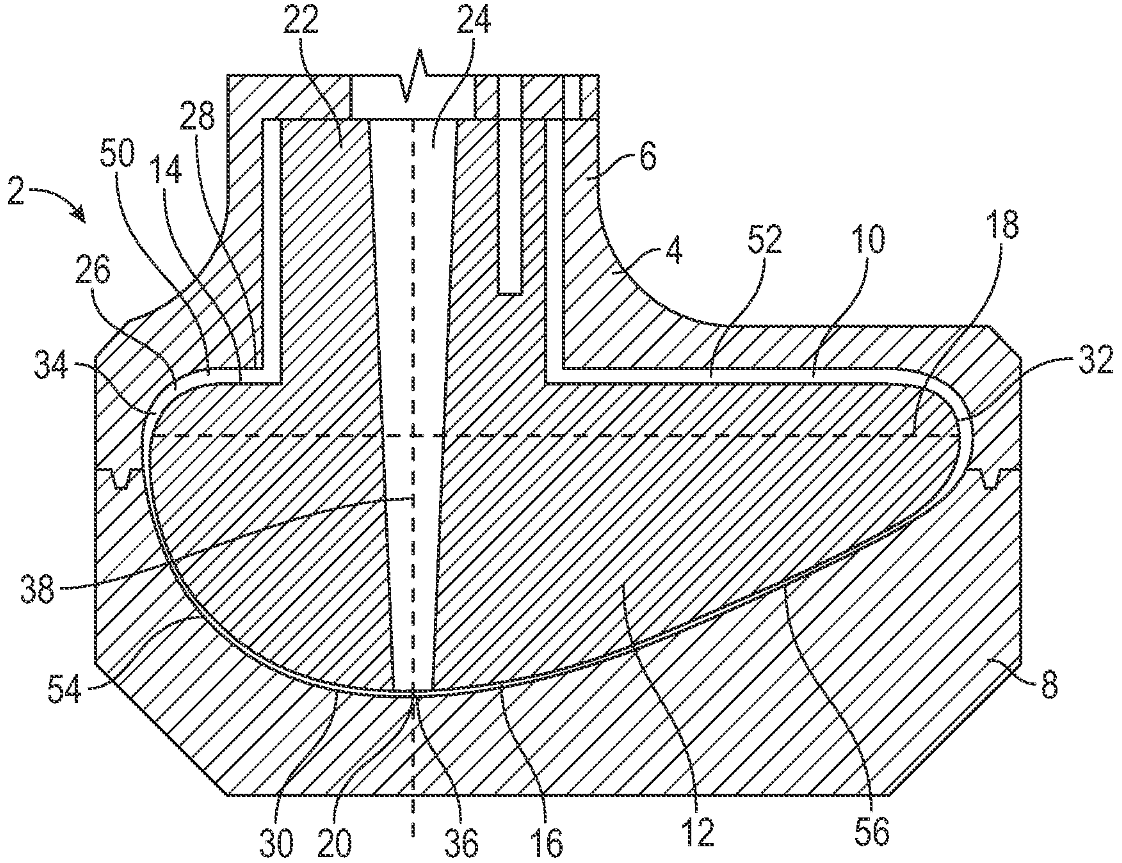
FIG. 2 is a cross-sectional side view of the breast implant injection mold of FIG. 1.

The methods of injection molding a breast implant disclosed herein require a breast implant injection mold. Referring to FIG. 1, a perspective view of a breast implant injection mold is illustrated. Referring to FIG. 2, a cross-sectional side view of the breast implant injection mold of FIG. 1 is illustrated. The breast implant injection mold 2 of FIG. 1 is a teardrop breast implant injection mold configured to mold a teardrop (or anatomical or non-round) shaped breast implant. As illustrated by FIGS. 1-2, the breast implant injection mold 2 includes an outer mold 4. In various implementations, the outer mold 4 may be stainless steel. In other implementations, the outer mold 4 may be made from a polymer based material, other metallic material, or other rigid material capable of producing an injection mold.

The outer mold 4 includes a first portion 6 and a second portion 8. The first portion 6 is configured to attach to the second portion 8. The first portion 6 and the second portion 8 form a cavity 10. The cavity 10 corresponds in shape and size to the breast implant configured to be injection molded in the breast implant injection mold 2. As illustrated by FIG. 2, the cavity has a teardrop shape which can in turn produce a teardrop shaped breast implant. In various implementations, the walls of the cavity may be smooth. In such implementations, the breast implant formed within the cavity may include a smooth outer surface. In other implementations, the walls of the cavity may be textured. In such implementations, the breast implant formed within the cavity may include a textured outer surface.

The breast implant injection mold 2 includes a core 12. The core 12 includes a back surface 14 and a front surface 16 opposite the back surface. The back surface 14 and front surface 16 are divided by a vertex boundary 18. Vertex boundary 18 is the boundary at which the curvature of the core 12 changes to sloping in towards the cusp 20 of the core 12. The cusp 20, as used herein, defines the front portion of the core furthest away from the back surface 14. As used herein, the back surface of the core is the surface of the core that forms a back wall of a breast implant. The back wall of a breast implant is the wall that is configured to be placed against the chest wall of a user when the breast implant is placed within a breast. The front surface of the core is the surface of the core that forms a front wall of a breast implant. The front wall of a breast implant is the wall that is configured to protrude away from the chest wall of a recipient when the breast implant is placed within a breast.

In various implementations, the back surface 14 of the core 12 may be substantially flat. The core 12 includes a neck 22 extending from the back surface 14. A sprue 24 extends through the neck 22 of the core 12. In various implementations, the neck 22 and sprue 24 of the core 12 may extend from the back surface 14 of the core opposite the cusp 20 of the core. In other implementations, the neck 22 and sprue 24 of the core 12 extend from the back surface 14 of the core at a location not opposite the cusp 20 of the core, or extend from a portion of the core different from the back surface.

When the core 12 is placed within the cavity 10 of the outer mold 4, the injection mold includes a volume 26 between the core 12 and the outer mold 4. Volume 26, as used herein with reference to the space between the core and the outer mold, refers to the space configured to be filled with injection molding material that forms the breast implant. Volume 26, as used herein, does not include the space between neck 22 of the core 12 and the outer mold as any injection molding material between the neck 22 and the outer mold will be trimmed from the breast implant.

The volume 26 includes a back portion 28, front portion 30, bottom portion 32, and top portion 34. The back portion 28 intersects with both the bottom portion 32 and the top portion 34 to form a back/bottom quadrant 50 and a back/top quadrant 52. The front portion 30 intersects with the bottom portion 32 and the top portion 34 to form a front/bottom quadrant 54 and also a front/top quadrant 56. The back portion 28 of the volume corresponds to the back surface 14 of the core 12. The back portion 28 and front portion 30 are divided by the vertex boundary 18. Vertex boundary 18 is also the boundary at which the curvature of the volume 26 changes to sloping in towards the cusp 36 of the volume 26. The cusp 36 is the portion of the volume 26 furthest from the back portion 28 of the volume. As used herein, the back portion 28 of the volume forms a back wall of a breast implant. The back wall of a breast implant is the wall that is configured to be placed against the chest wall of a user when the breast implant is placed within a breast. The front portion 30 of the volume 26 forms the front wall of a breast implant. The front wall of a breast implant is the wall that is configured to protrude away from the chest wall of a recipient when the breast implant is placed within a breast. The bottom portion 32 of the volume 26 is divided from the top portion 34 of the volume by boundary 38. Boundary 38 is substantially orthogonal to vertex boundary 18 and extends through the cusp 36 of the volume 26. The top portion 34 of the volume 26 is the portion configured to form a top portion of a breast implant. The top portion of the breast implant is the portion above the cusp of the breast implant. The bottom portion 32 of the volume 26 is the portion configured to form a bottom portion of a breast implant. The bottom portion of the breast implant is the portion below the cusp of the breast implant. Words used to describe positions or locations of portions of breast implants or portions of the injection mold used to form breast implants, such as, by non-limiting example, top, bottom, front, back, up, down, above, below, vertical, and horizontal are understood to indicate the position, orientation, or location corresponding to the breast implant when it is positioned in the breast of a recipient who is in an upright position. “Front” and “back” are understood as respectively corresponding with the surface of the breast implant that faces towards the front of the user when inserted within a breast and the surface of the breast implant that faces towards the back of the user when inserted within a breast. Accordingly, if the breast implant injection mold is rotated this does not change what may be referred to as, for example, the top portion of the volume.

The shape and size of the cavity 10 in conjunction with the shape and size of the core 12 determine the thickness of the volume 26 between the core 12 and the outer mold 4. In various implementations, a thickness of the volume between the core 12 and the outer mold 4 is consistent across the entire thickness. In other implementations, the thickness of the volume may vary. The thickness of the volume may include any thickness between 1-3 mm. In other implementations, the thickness may be less than 1 mm or more than 3 mm.

In implementations where the thickness of the volume varies, and as illustrated by FIG. 2, a first thickness between the core 12 and the outer mold 4 around a perimeter of the core at the vertex boundary 18 is greater than a second thickness between the core 12 and outer mold 4 at the front portion of the volume adjacent to the front surface of the core. In particular implementations, a first thickness between the core 12 and the outer mold 4 around a perimeter of the core at the vertex boundary 18 is greater than a second thickness between the core 12 and outer mold 4 at the cusp 36 of the volume 26. In various implementations, the increased thickness may extend around an entire perimeter of the volume 26 along the vertex boundary 18. In other implementations, the increased thickness may only extend around a portion of the perimeter of the volume 26 along the vertex boundary 18. In implementations where the volume 26 includes an increased thickness at the vertex boundary 18, the thickness of the volume may taper towards the cusp 36 of the volume 26.

Still referring to FIG. 2, in various implementations the back portion 28 of the volume 26 may include a thickness greater than the thickness of the front portion 30 of the volume. In particular implementations, only the back portion 28 of the volume 26 may include the increased thickness. In other implementations, the back portion 28 and portions of the front portion 30 may both include an increased thickness. In implementations of volumes having a back portion 28 thicker than the front portion 30, the entirety of the back portion 28 or just a portion of the back portion 28 may have the increased thickness. While FIG. 2 illustrates the entirety of the back portion 28 having the increased thickness, in other implementations the volume 26 may have an increased thickness around the vertex boundary 18 and the thickness may taper towards the cusp 36 and also towards the flat portion of the back portion 28.

Figure 3:
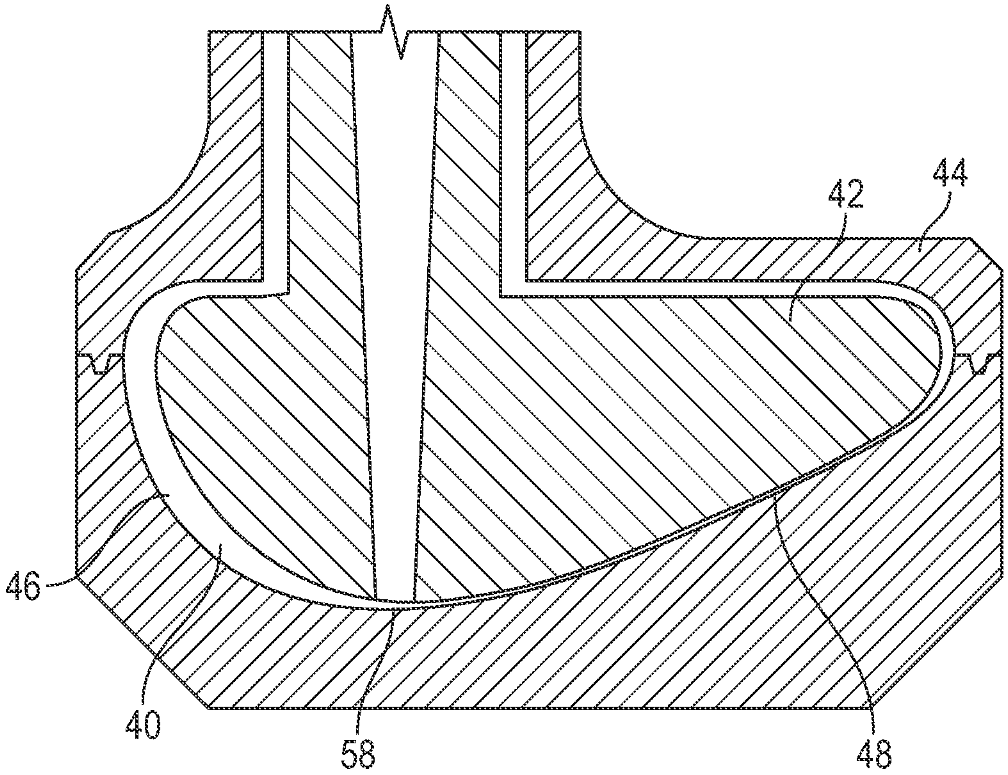
FIG. 3 is a cross-sectional side view of a second implementation of a breast implant injection mold.

Referring to FIG. 3, a cross-sectional side view of a second implementation of a breast implant injection mold is illustrated. In various implementations, the volume 40 formed between the core 42 and the outer mold 44 may include an increased thickness in the bottom portion 46 of the volume as compared to thickness of the front/top quadrant 48 of the volume. In such implementations, the increased thickness extends to the cusp 58 of the volume 40. The thickness may then transition from an increased thickness to a lesser thickness at the cusp 58 of the volume. In particular implementations, the entirety of the bottom portion 46 may include an increased thickness as compared to a thickness of the front/top quadrant 48.

Referring to FIGS. 4-8, various cross-sectional views of various cores are illustrated. The cores illustrated by FIGS. 4-8 do not include a neck, though it is understood that a neck would be included with the core if the core were used in a breast implant injection mold. Further, while the cores of FIGS. 4-8 all include recesses within the core, the magnitude of these recesses are exaggerated in order to more clearly illustrate how the cores might be modified in order to form volumes having varying thicknesses between the core and an outer mold.

Figure 4:
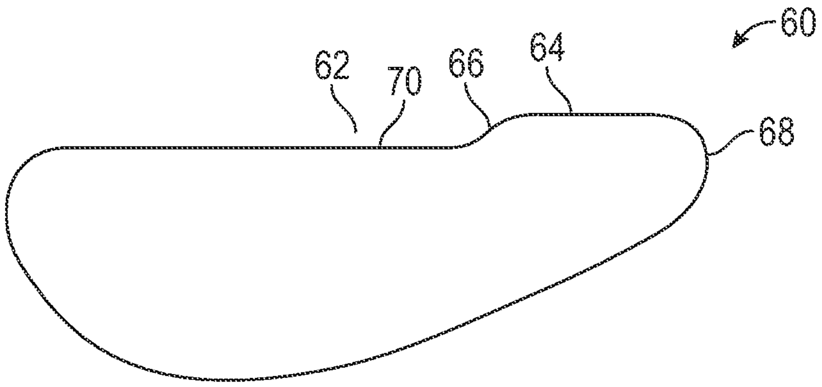
FIG. 4 is a cross sectional side view of a third implementation of a core.

Referring specifically to FIG. 4, a cross sectional side view of a third implementation of a core is illustrated. In various implementations, the core 60 may include a recess 62 formed into the back surface 64 of the core. In particular implementations, the edge 66 of the recess 62 may be formed between a top end 68 and a mid-point 70 of the back surface 64. In other implementations, the edge of the recess may be formed at any other location along the back surface 64 of the core. In still other implementations, the recess may be formed along an entirety of the back surface of the core.

Figure 5:
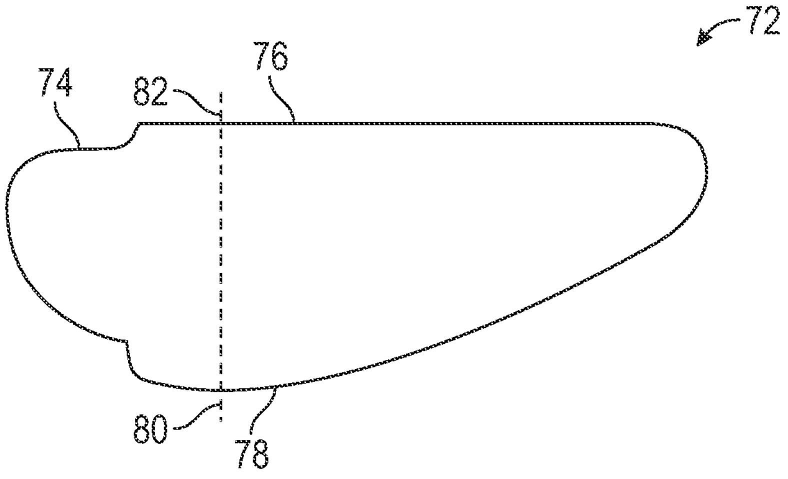
FIG. 5 is a cross sectional side view of a fourth implementation of a core.

Referring to FIG. 5, a cross sectional side view of a fourth implementation of a core is illustrated. In various implementations, the core 72 may include a recess 74 formed into both the back surface 76 and the front surface 78 of the core. In various implementations, the entirety of the recess 74 may be formed below the boundary 82 formed through the cusp 80. In other implementations, the recess may be formed above the boundary 82 on the back surface 76 and below the boundary on the front surface 78.

Figure 6:
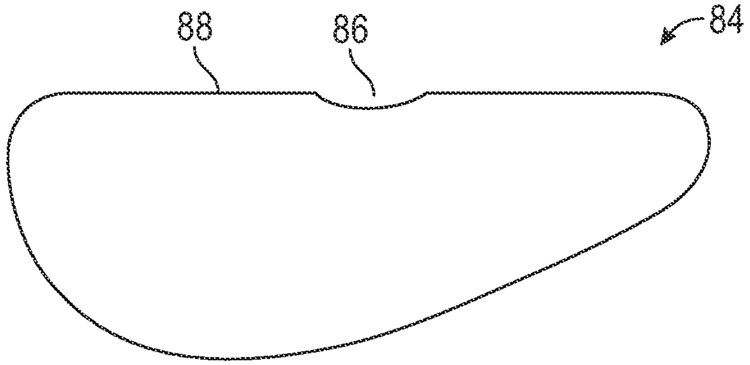
FIG. 6 is a cross sectional side view of a fifth implementation of a core.
Figure 7:
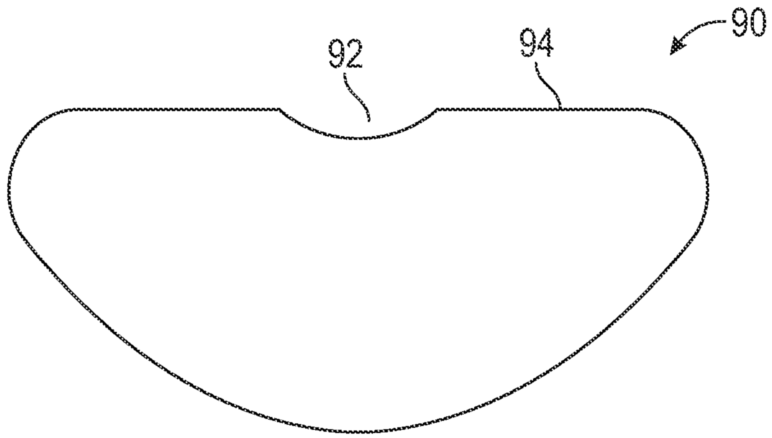
FIG. 7 is a cross sectional side view of a sixth implementation of a core.

Referring to FIG. 6, a cross sectional side view of a fifth implementation of a core is illustrated. In various implementations, the core 84 may include a recess 86 forming a channel in the back surface 88 of the core. While the channel of FIG. 6 is illustrated as extending across a width of the back surface 88 perpendicular to a longest length of the core, in other implementations the channel may extend through other portions of the back surface or may extend into the back surface in other patterns aside from a straight channel. For example, referring to FIG. 7, a cross sectional side view of a sixth implementation of a core is illustrated. The core 90 of FIG. 7 is shown in a cross sectional view taken across a width of the core perpendicular to the longest length of the core. In other words, the core 90 of FIG. 7 is illustrated as viewed from the bottom portion of the core. In turn, while the core 90 of FIG. 7 looks like it corresponds to a round implant, because it is viewed from the bottom portion it can correspond to a teardrop shaped implant. As illustrated by FIG. 7, in various implementations the core 90 may include a recess 92 forming a channel in the back surface 94 of the core. The recess 92 may extend parallel to the longest length of the core 90. In various implementations, the recess 92 may extend across an entire length of the back surface 94 or just partially across the length of the back surface. While the recess 92 of FIG. 7 is illustrated as centered in the back surface 94, in other implementations the recess may be off-centered in the back surface. In various implementations, the core may include two intersecting channels (such as the channels illustrated in both FIGS. 6 and 7). In other implementations, the core may include only a single channel.

Figure 8:
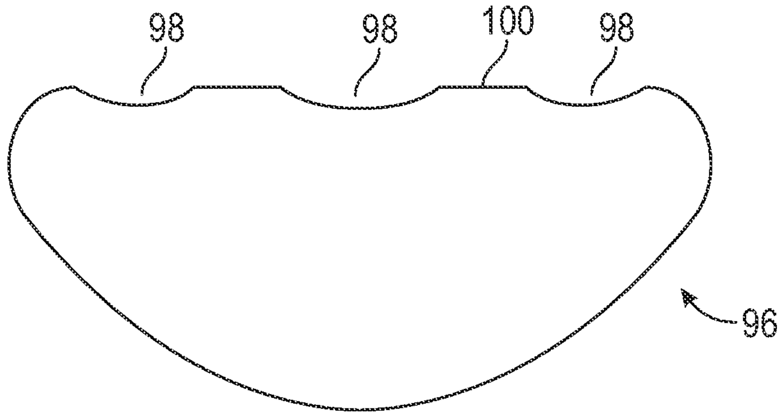
FIG. 8 is a cross sectional side view of a seventh implementation of a core.

Referring to FIG. 8, a cross sectional side view of a seventh implementation of a core is illustrated. Like the core of FIG. 7, the core 96 of FIG. 8 is shown in a cross sectional view taken across a width of the core perpendicular to the longest length of the core. In turn, while the core 96 of FIG. 8 looks like it corresponds to a round implant, because it is viewed from the bottom portion it can correspond to a teardrop shaped implant. As illustrated by FIG. 8, in various implementations the core 96 may include a plurality of recesses 98 forming a plurality of channels in the back surface 100 of the core. While FIG. 8 illustrates three channels, other implementations may include more than three channels or only two channels. The recesses 98 may extend parallel to the longest length of the core 96. In various implementations, the recesses 98 may extend across an entire length of the back surface 100 or just partially across the length of the back surface.

In other implementations the back surface of a core may include other varying patterns of channels than what is illustrated by FIGS. 4-8.

While FIGS. 4-8 illustrate the core as having recesses formed therein which provide for varying thicknesses of a volume between a core and an outer mold, in other implementations the sidewall of the cavity of the outer mold may include recesses formed therein which provide for varying thicknesses of the volume between the core and the outer mold.

Figure 9:
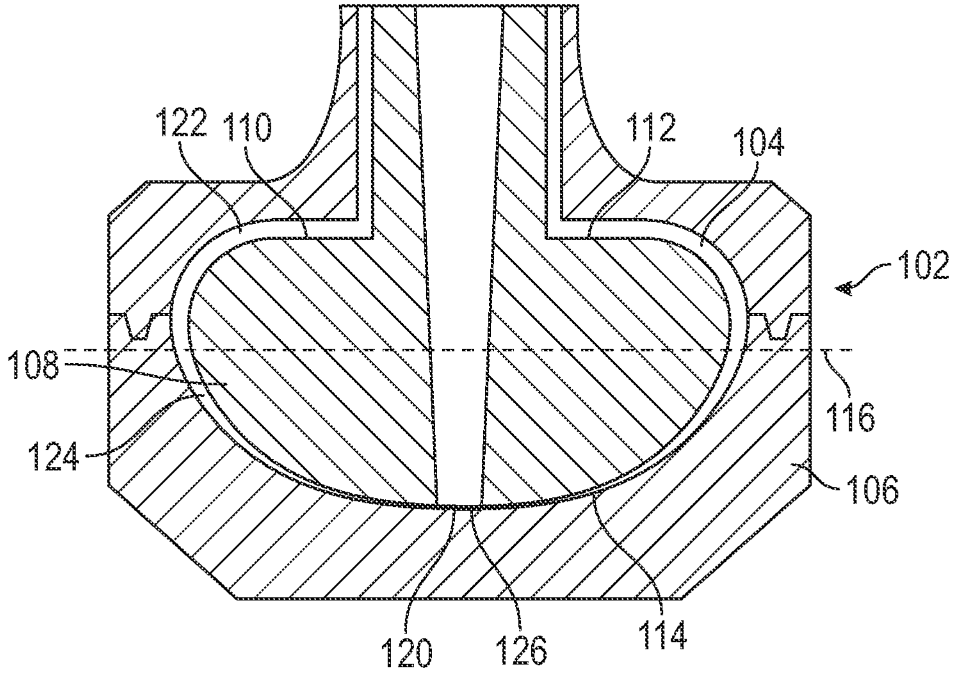
FIG. 9 is a cross sectional side view of a third implementation of a breast implant injection mold.

Referring to FIG. 9, a cross sectional side view of a third implementation of a breast implant injection mold is illustrated. The breast implant injection mold 102 of FIG. 9 is a round breast implant injection mold configured to mold a round shaped breast implant. The breast implant injection mold 102 to the breast implant injection mold of FIG. 2 with the difference being that the cavity 104 of the outer mold 106 and the core 108 are round, or substantially form a symmetrical hemispherical shape.

The core includes a back surface 112 and a front surface 114 opposite the back surface. The back surface 112 and front surface 114 are divided by a vertex boundary 116. Vertex boundary 116 is the boundary at which the curvature of the core 108 changes to sloping in towards the cusp 120 of the core 108. The cusp 120, as used herein, defines the front portion of the core furthest away from the back surface 112.

The breast implant injection mold 102 includes a volume 110 between the core 108 and the outer mold 106. The volume 110 includes a back portion 122 and a front portion 124. The back portion 122 of the volume and the front portion 124 of the volume are divided by the vertex boundary 116. Vertex boundary 116 is also the boundary at which the curvature of the volume 110 changes to sloping in towards the cusp 126 of the volume 110. The cusp 126 is the portion of the volume 110 furthest from the back portion 122 of the volume.

In various implementations, a thickness of the volume 110 between the core 108 and the outer mold 106 is consistent across the entire thickness. In other implementations, the thickness of the volume 110 may vary. The thickness of the volume may include any thickness disclosed herein.

In implementations where the thickness of the volume varies, and as illustrated by FIG. 9, a first thickness between the core 108 and the outer mold 106 around a perimeter of the core at the vertex boundary 116 is greater than a second thickness between the core 108 and outer mold 106 at the front portion 124. In various implementations, the portions of the volume having the increased thickness may extend around an entire perimeter of the volume 110 along the vertex boundary 116. In other implementations, the portion having the increased thickness may only extend around a portion of the perimeter of the volume 110 along the vertex boundary 116. In implementations where the volume 110 includes an increased thickness at the vertex boundary 116, the thickness of the volume may taper towards the cusp 126 of the volume 110.

Still referring to FIG. 9, in various implementations the back portion 122 of the volume 110, including the flat portion of the back portion, may include a thickness greater than the thickness of the front portion 124 of the volume. In particular implementations, only the back portion 122 of the volume 110 may include the increased thickness. In other implementations, the back portion 122 and portions of the front portion 124 may both include an increased thickness. In implementations of volumes having a back portion 122 thicker than the front portion 124, and as illustrated by FIG. 9, the entirety of the back portion 122 may have a thickness greater than the thickness at the cusp 126 of the volume.

Figure 10:
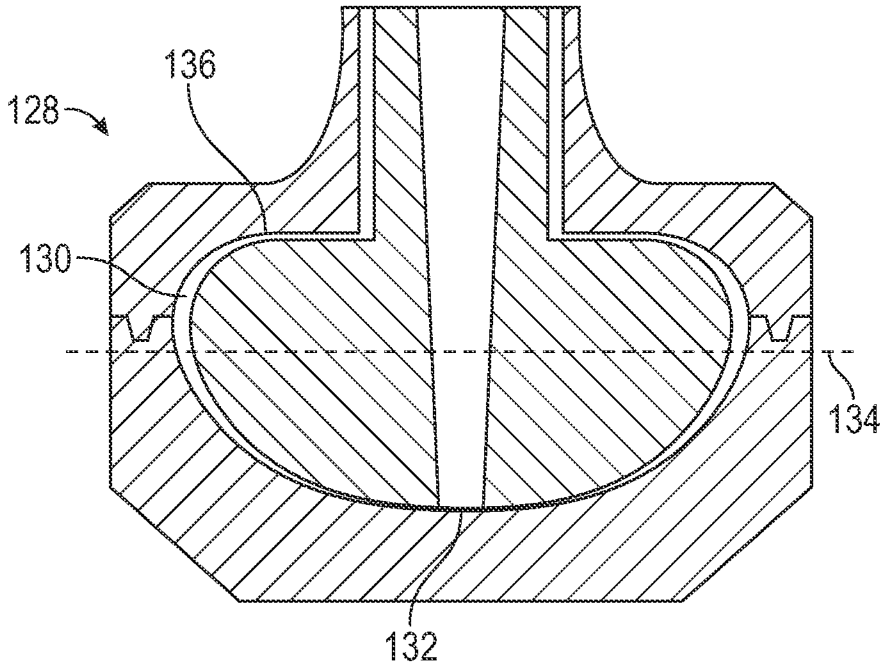
FIG. 10 is a cross-sectional side view of a fourth implementation of a breast implant injection mold.

Referring to FIG. 10, a cross-sectional side view of a fourth implementation of a breast implant injection mold is illustrated. The breast implant injection mold 128 is similar to the breast implant injection mold of FIG. 9 with the only difference being that only portions of the back portion 136 of the volume 130 have an increased thickness as compared to the thickness of the cusp 132 of the volume. As illustrated by FIG. 10, the volume 130 may have an increased thickness around the vertex boundary 134 and the thickness may taper towards the cusp 132 and also towards the flat portion of the back portion 136.

In various implementations, the core of a round implant may include recesses formed therein which result in varying thicknesses between the core of the breast implant injection mold and the outer mold. In particular implementations, the core used in a round breast implant injection mold may include one or more recesses that form channels similar to the recesses illustrated by FIGS. 7-8. In particular implementations, the back surface of a core of a round breast implant injection mold may include a plurality of intersecting channels. In other implementations, the back surface of a core may include recesses having a circular perimeter entirely contained in the flat portion of the back surface of the core. In such implementations, the recesses may form a ring or a complete circle. In other implementations, the back surface of the core may include multiple channels forming multiple rings, a combination of channels forming rings and recesses forming other shapes, or any other type of recess.

Figure 11:
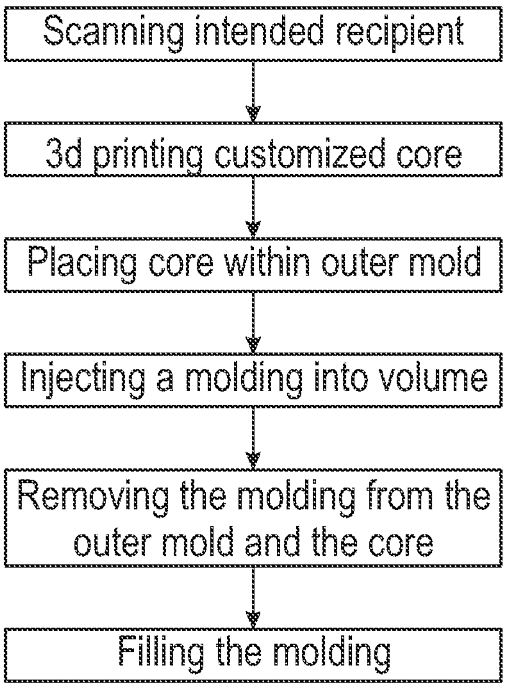
FIG. 11 is a flow chart illustrating the method of injection molding a breast implant.

Referring to FIG. 11, a flow chart illustrating a method of injection molding a breast implant is illustrated. In various implementations the method of injection molding a breast implant may first include scanning an intended recipient of a breast implant. Scanning the intended recipient may determine what kind of breast implant the intended recipient needs based upon needs or desired aesthetics. For example, the intended recipient may have a very thin layer of breast tissue which may require a breast implant having a reinforced structure in portions of the breast implant to compensate for the thin layer of breast tissue and reduce the likelihood of buckling or rippling of the breast implant.

The method of injection molding a breast implant includes selecting an outer mold having a cavity corresponding to a desired shape and size of the breast implant to be injection molded. In other implementations, the method may include forming an outer mold with a cavity having the desired shape and size of the breast implant to be injection molded. The outer mold would be formed through a separate injection mold process or may be 3D printed using any 3D printing technique disclosed herein. In implementations where the outer mold includes a custom cavity, the method may include customizing the outer mold to form recesses or depressions within the cavity sidewall in order to increase a thickness of a volume between the outer mold and the core. In various implementations, only the outer mold may be customized, only the core may be customized, or both the outer mold and the core may be customized.

The method of injection molding a breast implant may include forming a customized core based on the scan of the intended recipient. In various implementations the method may include converting the scan from scanning the intended recipient to a 3D model of a breast implant. The method may then include creating a file, such as an STL file, for 3D printing (if 3D printing is used) the customized core. The formed core may be the same as or similar to any core described herein. Customization of the core entails forming the core in a manner that results in a thicker volume between the core and the outer mold at specific portions of the volume. In various implementations, the core may be 3D printed. In such implementations, the core may be 3D printed using, by non-limiting example, a stereolithography printing technique or a fused deposition modeling technique. In other implementations, the core may be formed through a separate injection molding process. In still other implementations, the customized core may be customized by either of forming a standard core or taking an existing standard core and then removing portions of the core to result in the volume between the core and the outer mold having portions with an increased thickness based upon the intended recipients needs and desired aesthetics.

The method of injection molding a breast implant may include placing the core within the outer mold and creating a volume between the core of the outer mold. The volume may include varying thicknesses the same as or similar to any volume disclosed herein.

The method of injection molding a breast implant includes injecting a molding into the volume between the core and the outer mold. In various implementations, the molding may be silicone. In other implementations, the molding may be a non-silicone material with sufficient flexibility to form a breast implant. The method includes curing the molding. In particular implementations, the molding may be cured through cooling.

Figure 12:
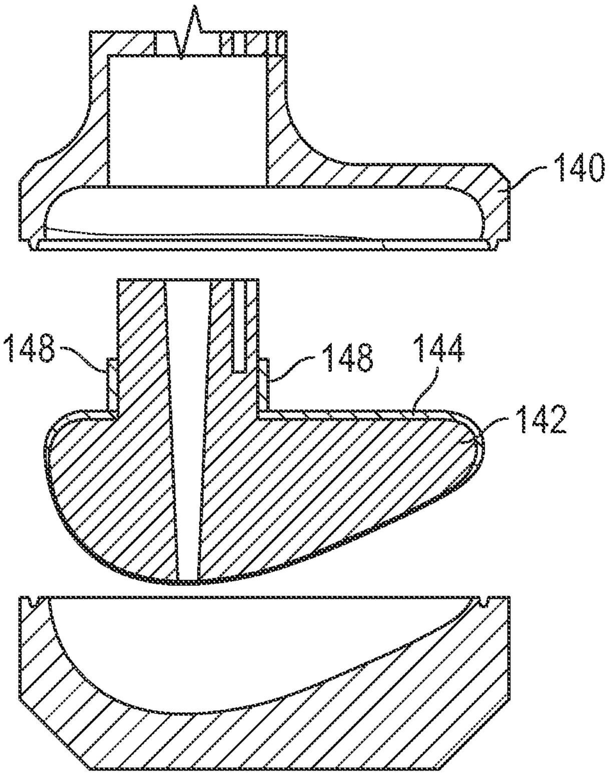
FIG. 12 is a cross-sectional side view of a breast implant injection mold having the core separated from the outer mold.

The method of injection molding a breast implant includes removing the cured molding and the core from the outer mold. Referring to FIG. 12, a cross-sectional side view of a breast implant injection mold having the core separated from the outer mold is illustrated. As illustrated, the outer mold 140 is separated to allow for the core 142 having a molding 144 coupled thereto to be removed from the outer mold. Particular thickness of the cured molding corresponds to the volume between the core 142 and the outer mold 140.

Figure 13:
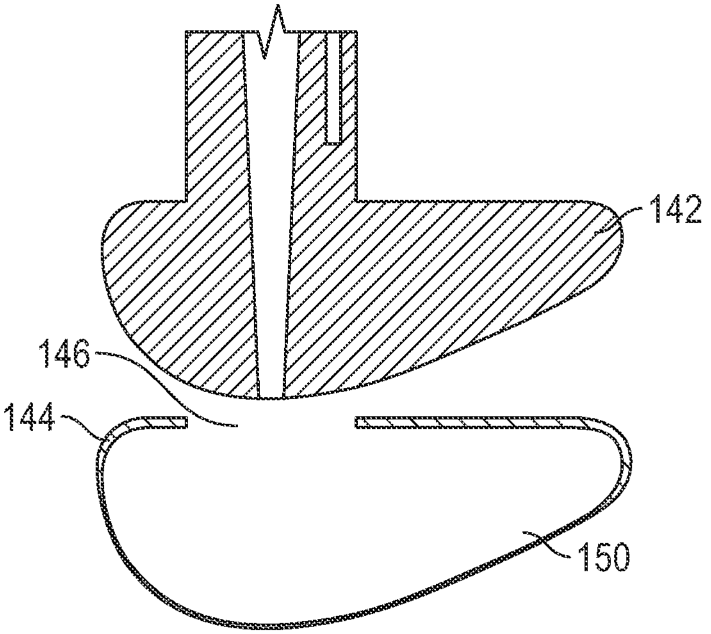
FIG. 13 is a cross-sectional side view of a molding compound separated from the core of the breast implant injection mold of FIG. 12.

Referring to FIG. 13, a cross-sectional side view of a molding compound separated from the core of the breast implant injection mold of FIG. 12 is illustrated. The method of injection molding a breast implant includes removing the core 142 from the molding 144. The core 142 may be removed through the opening 146. In various implementations, the method may also include removing excess portions of molding (for example, portions 148 in FIG. 12) from the molding configured to form the breast implant.

In various implementations where the sidewalls of the cavity of the outer mold are not sufficiently smooth and result in a textured cured outer surface of the molding, the method may include smoothing the outer surface of the molding 144. Smoothing may occur either before the molding is removed from the core or after the molding is removed from the core. Inasmuch as smoothing removes a small portion of the outer surface of the molding, in various implementations the method of varying the thickness of the sidewalls of the breast implant could also include thinning portions of the molding after the molding is cured using a similar technique to the technique used to smooth the outer surface of the breast implant.

Figure 14:
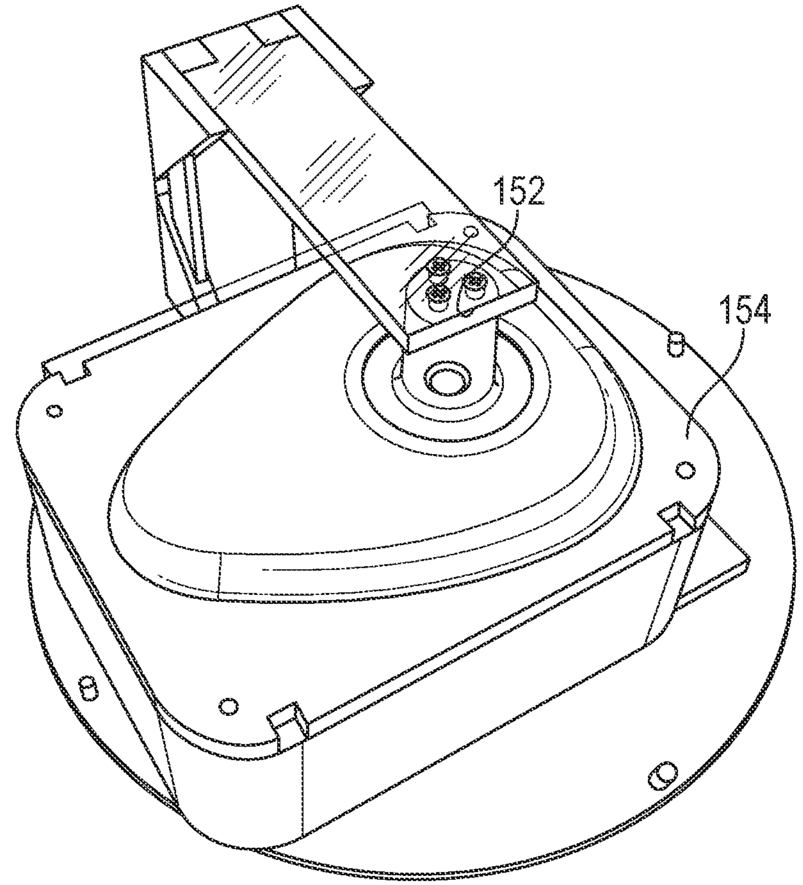
FIG. 14 is a perspective view of a cradle and back-fill jig.

Referring to FIG. 14, a perspective view of a cradle and a back-fill jig is illustrated. In various implementations, the method of injection molding a breast implant may include placing the molding material within a cradle 154 configured to help maintain the form of the cured molding. The method may also include using a back-fill jig to hold up the cured molding and prevent the molding from collapsing into the volume within the molding. Use of the cradle and the backfill jig may allow for a fuller fill of the breast implant which may in turn reduce the likelihood of rippling or buckling of the breast implant.

In various implementations, the method of injection molding the breast implant includes closing the opening 146 in the molding with a patch. In implementations utilizing the cradle and back-fill jig, the patch may be placed over the opening before the molding is placed in the cradle or after the molding is placed in the cradle. The method may include filling the volume 150 within the molding with a fluid. The fluid may include, by nonlimiting example, a silicone-gel, saline, or any other fluid or semi-fluid material used to fill a breast implant. The volume may be filled prior to placing the patch over the opening 146 or after the patch is placed over the opening.

While the method disclosed herein describes injection molding a customized breast implant based upon a particular recipient's needs and desired aesthetics, in other implementations the method may include injection molding a breast implant utilizing any of the methods or related breast implant injection mold components described herein to form a breast implant that may not necessarily be tailored to a particular individual. In turn, the method of injection molding a breast implant may be performed without scanning an intended recipient beforehand.

The methods of injection molding breast implants disclosed herein may result in the production of breast implants with the sidewalls having varying thicknesses. The thicker portions of the sidewalls may prevent buckling and rippling of the breast implant when placed within a breast. Further, methods disclosed herein may result in breast implants having sidewalls with varying thicknesses that result in increased stability of the breast implant. For example, the implementations of breast implants injection molded that have a volume between the core of the outer mold with an increased thickness around a perimeter of the core at the vertex boundary have a ring of increased thickness around the perimeter of the implant. This increased thickness may help the breast implant maintain form and reduce the likelihood of the breast implant flipping inasmuch as the back of the breast implant may be more resistant to folding. In other implementations of methods disclosed herein, the methods may produce a breast implant with sidewalls having varying thicknesses that may alter the weight distribution of the implant. By modifying the weight distribution, the implant may be less likely to rotate or flip when placed within a breast. Further, unwanted rotation or flipping of breast implants may be achieved with smooth breast implants as well as textured breast implants.

In places where the description above refers to particular implementations of methods of injection molding breast implants, breast implant injection molds, and implementing components, sub-components, methods and sub-methods, it should be readily apparent that a number of modifications may be made without departing from the spirit thereof and that these implementations, implementing components, sub-components, methods and sub-methods may be applied to other methods of injection molding breast implants and breast implant injection molds.

What is claimed is:

1. A method of injection molding a breast implant comprising:

placing a core within an outer mold comprising a cavity, the cavity corresponding in shape and size to a breast implant;

injecting a molding into a volume between the core and outer mold;

removing the molding from the core and outer mold; and filling the molding to form the breast implant;

wherein a first thickness of the volume between the core and the outer mold around a perimeter of the core at a vertex boundary is greater than a second thickness of the volume between the core and the outer mold at a cusp of the core; and wherein the outer mold covers a back surface of the core.

2. The method of claim 1, wherein the cavity corresponds in shape and size to a round breast implant.

3. The method of claim 1, wherein the cavity corresponds in shape and size to a teardrop shaped breast implant.

4. The method of claim 1, wherein the cavity comprises a smooth sidewall configured to form a smooth breast implant.

5. The method of claim 1, further comprising smoothing the breast implant after removing the molding from the core and the outer mold.

6. The method of claim 1, further comprising placing the molding into a cradle prior to filling the molding and attaching a back-fill jig to the molding.

7. The method of claim 1, wherein a back portion of the core comprises a channel.

8. A method of injection molding a breast implant comprising:

scanning an intended recipient of a breast implant;

3D printing a customized core, based on the intended recipient, configured to be placed within an outer mold comprising a cavity, the cavity corresponding in shape and size to a breast implant;

placing the customized core into the cavity;

injecting a molding into a volume between the customized core and outer mold, wherein the outer mold covers a back surface of the customized core;

removing the molding from the customized core and outer mold; and filling the molding to form the breast implant;

wherein the customized core comprises a back portion opposite a front portion, wherein the back portion is divided from the front portion by a vertex boundary;

wherein a consistency of a thickness of the volume between the customized core and outer mold varies depending upon the intended recipient.

9. The method of claim 8, wherein the cavity corresponds in shape and size to a round breast implant.

10. The method of claim 8, wherein the cavity corresponds in shape and size to a teardrop shaped breast implant.

11. The method of claim 8, wherein the outer mold is made from steel.

12. The method of claim 8, further comprising smoothing the breast implant after removing the molding from the customized core and the outer mold.

13. The method of claim 8, wherein the back portion of the customized core comprises a channel.

* * * * *